US008956350B2

(12) United States Patent
Buysse et al.

(10) Patent No.: US 8,956,350 B2
(45) Date of Patent: *Feb. 17, 2015

(54) THERMAL FEEDBACK SYSTEMS AND METHODS OF USING THE SAME

(71) Applicant: Covidien LP, Mansfield, MA (US)

(72) Inventors: Steven P. Buysse, Niwot, CO (US); Casey M. Ladtkow, Erie, CO (US); Brandon Gay, Superior, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/066,050

(22) Filed: Oct. 29, 2013

(65) Prior Publication Data
US 2014/0058384 A1 Feb. 27, 2014

Related U.S. Application Data

(60) Continuation of application No. 13/539,725, filed on Jul. 2, 2012, now Pat. No. 8,568,402, which is a division of application No. 12/023,606, filed on Jan. 31, 2008, now Pat. No. 8,211,099.

(60) Provisional application No. 60/887,537, filed on Jan. 31, 2007.

(51) Int. Cl.
A61B 18/18 (2006.01)
A61B 5/00 (2006.01)
(Continued)

(52) U.S. Cl.
CPC ........... *A61B 5/4836* (2013.01); *A61B 18/1477* (2013.01); *A61B 5/015* (2013.01);
(Continued)

(58) Field of Classification Search
USPC ...................................... 606/32–35
See application file for complete search history.

(56) References Cited

U.S. PATENT DOCUMENTS 2,031,682 A 2/1936 Wappler et al.
D223,367 S 4/1972 Kountz
(Continued)

FOREIGN PATENT DOCUMENTS

CN 1103807 A 6/1995
DE 390937 C 3/1924
(Continued)

OTHER PUBLICATIONS

Michael Choti, "Abdominoperineal Resection with the LigaSure.TM. Vessel Sealing System and LigaSure.TM. Atlas 20 cm Open Instrument" Innovations That Work, Jun. 2003.
(Continued)

*Primary Examiner* — Linda Dvorak
*Assistant Examiner* — Amanda Scott

(57) ABSTRACT

A system for providing feedback during an electrosurgical procedure on a target tissue is provided. The system includes an electrosurgical energy source; an electrode probe assembly connected to the electrosurgical energy source, wherein the electrode probe assembly includes at least one electrode assembly having a needle configured to deliver electrosurgical energy to the target tissue; at least one thermal feedback assembly connected to the electrosurgical energy source, wherein each thermal feedback assembly includes at least one temperature sensor assembly; and a hub configured to selectively support the electrode probe assembly and each thermal feedback assembly such that the needle of the electrode probe assembly and each temperature sensor assembly of each thermal feedback assembly are proximate one another when disposed proximate the target tissue.

19 Claims, 6 Drawing Sheets

(51) Int. Cl.
  *A61B 18/14* (2006.01)
  *A61B 5/01* (2006.01)
  *A61B 18/12* (2006.01)
  *A61B 18/00* (2006.01)
  *A61B 19/00* (2006.01)

(52) U.S. Cl.
  CPC ............ *A61B 5/743* (2013.01); *A61B 18/1206* (2013.01); *A61B 18/18* (2013.01); *A61B 2018/00702* (2013.01); *A61B 2018/00791* (2013.01); *A61B 2018/00797* (2013.01); *A61B 2018/00815* (2013.01); *A61B 2018/00821* (2013.01); *A61B 2019/5236* (2013.01); *A61B 2019/5238* (2013.01); *A61B 2019/524* (2013.01); *A61B 2019/5276* (2013.01)
  USPC .............................................. 606/34; 606/41

(56) References Cited

U.S. PATENT DOCUMENTS

| | | |
|---|---|---|
| 4,074,718 A | 2/1978 | Morrison, Jr. |
| 4,075,497 A | 2/1978 | Kraus |
| 4,215,275 A | 7/1980 | Wickersheim |
| D263,020 S | 2/1982 | Rau, III |
| D266,842 S | 11/1982 | Villers et al. |
| 4,375,220 A | 3/1983 | Matvias |
| 4,411,266 A | 10/1983 | Cosman |
| 4,448,547 A | 5/1984 | Wickersheim |
| D278,306 S | 4/1985 | McIntosh |
| 4,560,286 A | 12/1985 | Wickersheim |
| 4,565,200 A | 1/1986 | Cosman |
| 4,576,177 A | 3/1986 | Webster, Jr. |
| 4,608,977 A | 9/1986 | Brown |
| 4,662,383 A | 5/1987 | Sogawa et al. |
| 4,739,759 A | 4/1988 | Rexroth et al. |
| D295,893 S | 5/1988 | Sharkany et al. |
| D295,894 S | 5/1988 | Sharkany et al. |
| 4,752,141 A | 6/1988 | Sun et al. |
| 4,832,024 A | 5/1989 | Boussignac et al. |
| 4,880,719 A | 11/1989 | Murofushi et al. |
| 4,883,354 A | 11/1989 | Sun et al. |
| 4,961,435 A | 10/1990 | Kitagawa et al. |
| 4,966,597 A | 10/1990 | Cosman |
| 4,988,212 A | 1/1991 | Sun et al. |
| 4,993,430 A | 2/1991 | Shimoyama et al. |
| 5,029,588 A | 7/1991 | Yock et al. |
| 5,103,804 A | 4/1992 | Abele et al. |
| 5,225,741 A | 7/1993 | Auld, Jr. et al. |
| 5,230,623 A | 7/1993 | Guthrie et al. |
| 5,233,515 A | 8/1993 | Cosman |
| 5,246,438 A | 9/1993 | Langberg |
| 5,267,994 A | 12/1993 | Gentelia et al. |
| 5,281,213 A | 1/1994 | Milder et al. |
| 5,323,778 A | 6/1994 | Kandarpa et al. |
| 5,330,470 A | 7/1994 | Hagen |
| 5,330,518 A | 7/1994 | Neilson et al. |
| 5,334,193 A | 8/1994 | Nardella |
| 5,342,357 A | 8/1994 | Nardella |
| 5,348,554 A | 9/1994 | Imran et al. |
| 5,370,675 A | 12/1994 | Edwards et al. |
| D354,218 S | 1/1995 | Van de Peer |
| 5,383,876 A | 1/1995 | Nardella |
| 5,383,917 A | 1/1995 | Desai et al. |
| 5,385,148 A | 1/1995 | Lesh et al. |
| 5,403,311 A * | 4/1995 | Abele et al. .................... 606/49 |
| 5,409,000 A | 4/1995 | Imran |
| 5,409,006 A | 4/1995 | Buchholtz et al. |
| 5,417,686 A | 5/1995 | Peterson et al. |
| 5,433,739 A | 7/1995 | Sluijter et al. |
| 5,437,662 A | 8/1995 | Nardella |
| 5,458,597 A | 10/1995 | Edwards et al. |
| 5,462,521 A | 10/1995 | Brucker et al. |
| 5,472,441 A | 12/1995 | Edwards et al. |
| 5,490,850 A | 2/1996 | Ellman et al. |
| 5,496,312 A | 3/1996 | Klicek |
| 5,500,012 A | 3/1996 | Brucker et al. |
| 5,520,684 A | 5/1996 | Imran |
| 5,536,267 A | 7/1996 | Edwards et al. |
| 5,571,147 A | 11/1996 | Sluijter et al. |
| 5,588,432 A | 12/1996 | Crowley |
| 5,599,345 A | 2/1997 | Edwards et al. |
| 5,643,197 A | 7/1997 | Brucker et al. |
| 5,647,871 A | 7/1997 | Levine et al. |
| 5,662,111 A | 9/1997 | Cosman |
| 5,683,384 A | 11/1997 | Gough et al. |
| 5,688,267 A | 11/1997 | Panescu et al. |
| 5,735,847 A | 4/1998 | Gough et al. |
| 5,775,338 A | 7/1998 | Hastings |
| 5,792,146 A | 8/1998 | Cosman |
| 5,848,967 A | 12/1998 | Cosman |
| 5,849,011 A | 12/1998 | Jones et al. |
| 5,868,740 A | 2/1999 | LeVeen et al. |
| 5,897,552 A * | 4/1999 | Edwards et al. .................. 606/31 |
| 5,921,982 A | 7/1999 | Lesh et al. |
| 5,943,719 A | 8/1999 | Feldman et al. |
| 5,951,546 A | 9/1999 | Lorentzen |
| 6,001,093 A | 12/1999 | Swanson et al. |
| 6,006,126 A | 12/1999 | Cosman |
| 6,053,912 A | 4/2000 | Panescu et al. |
| D424,693 S | 5/2000 | Pruter |
| D424,694 S | 5/2000 | Tetzlaff et al. |
| D425,201 S | 5/2000 | Tetzlaff et al. |
| 6,059,780 A | 5/2000 | Gough et al. |
| 6,061,551 A | 5/2000 | Sorrells et al. |
| 6,071,281 A | 6/2000 | Burnside et al. |
| 6,074,389 A | 6/2000 | Levine et al. |
| 6,080,149 A | 6/2000 | Huang et al. |
| 6,080,150 A | 6/2000 | Gough |
| 6,106,524 A | 8/2000 | Eggers et al. |
| 6,113,591 A * | 9/2000 | Whayne et al. .................. 606/34 |
| 6,132,426 A | 10/2000 | Kroll |
| 6,146,380 A | 11/2000 | Racz et al. |
| 6,161,048 A | 12/2000 | Sluijter et al. |
| 6,162,216 A | 12/2000 | Guziak et al. |
| 6,203,541 B1 | 3/2001 | Keppel |
| 6,241,725 B1 | 6/2001 | Cosman |
| 6,246,912 B1 | 6/2001 | Sluijter et al. |
| 6,277,116 B1 * | 8/2001 | Utely et al. ...................... 606/42 |
| 6,287,305 B1 | 9/2001 | Heim et al. |
| D449,886 S | 10/2001 | Tetzlaff et al. |
| 6,306,132 B1 | 10/2001 | Moorman et al. |
| 6,337,998 B1 | 1/2002 | Behl et al. |
| D457,958 S | 5/2002 | Dycus et al. |
| D457,959 S | 5/2002 | Tetzlaff et al. |
| 6,405,733 B1 | 6/2002 | Fogarty et al. |
| 6,432,070 B1 | 8/2002 | Talish et al. |
| 6,478,793 B1 | 11/2002 | Cosman et al. |
| 6,500,172 B1 | 12/2002 | Panescu et al. |
| 6,506,189 B1 | 1/2003 | Rittman, III et al. |
| 6,530,922 B2 | 3/2003 | Cosman et al. |
| 6,537,272 B2 | 3/2003 | Christopherson et al. |
| 6,551,311 B2 | 4/2003 | Lee et al. |
| 6,562,033 B2 | 5/2003 | Shah et al. |
| 6,569,159 B1 | 5/2003 | Edwards et al. |
| 6,575,969 B1 * | 6/2003 | Rittman et al. .................. 606/41 |
| 6,587,731 B1 * | 7/2003 | Ingle et al. ..................... 607/101 |
| 6,605,085 B1 | 8/2003 | Edwards |
| 6,613,047 B2 | 9/2003 | Edwards |
| 6,622,731 B2 | 9/2003 | Daniel et al. |
| 6,673,070 B2 | 1/2004 | Edwards et al. |
| D487,039 S | 2/2004 | Webster et al. |
| 6,685,729 B2 | 2/2004 | Gonzalez |
| 6,699,243 B2 | 3/2004 | West et al. |
| 6,783,523 B2 | 8/2004 | Qin et al. |
| 6,786,905 B2 | 9/2004 | Swanson et al. |
| D496,997 S | 10/2004 | Dycus et al. |
| 6,807,444 B2 | 10/2004 | Tu et al. |
| D499,181 S | 11/2004 | Dycus et al. |
| 6,918,907 B2 | 7/2005 | Kelly et al. |
| 7,008,421 B2 | 3/2006 | Daniel et al. |
| D525,361 S | 7/2006 | Hushka |
| D531,311 S | 10/2006 | Guerra et al. |
| 7,131,970 B2 | 11/2006 | Moses et al. |

(56) References Cited

U.S. PATENT DOCUMENTS

| | | |
|---|---|---|
| 7,137,980 B2 | 11/2006 | Buysse et al. |
| D533,942 S | 12/2006 | Kerr et al. |
| 7,150,749 B2 | 12/2006 | Dycus et al. |
| D535,027 S | 1/2007 | James et al. |
| 7,156,842 B2 | 1/2007 | Sartor et al. |
| 7,156,846 B2 | 1/2007 | Dycus et al. |
| 7,169,146 B2 | 1/2007 | Truckai et al. |
| 7,179,255 B2 | 2/2007 | Lettice et al. |
| 7,186,222 B1 | 3/2007 | Callister et al. |
| D541,418 S | 4/2007 | Schechter et al. |
| 7,207,989 B2 | 4/2007 | Pike, Jr. et al. |
| D541,938 S | 5/2007 | Kerr et al |
| 7,218,958 B2 | 5/2007 | Rashidi |
| 7,220,260 B2 | 5/2007 | Fleming et al. |
| 7,235,070 B2 | 6/2007 | Vanney |
| 7,235,073 B2 | 6/2007 | Levine et al. |
| 7,238,184 B2 | 7/2007 | Megerman et al. |
| 7,252,667 B2 | 8/2007 | Moses et al. |
| 7,264,619 B2 | 9/2007 | Venturelli |
| 7,278,991 B2 | 10/2007 | Morris et al. |
| 7,282,049 B2 | 10/2007 | Orszulak et al. |
| 7,294,127 B2 | 11/2007 | Leung et al. |
| 7,294,143 B2 | 11/2007 | Francischelli |
| 7,302,285 B2 | 11/2007 | Fuimaono et al. |
| 7,303,558 B2 | 12/2007 | Swanson |
| 7,331,947 B2 | 2/2008 | McGuckin, Jr. et al. |
| RE40,156 E | 3/2008 | Sharps et al. |
| D564,662 S | 3/2008 | Moses et al. |
| 7,341,586 B2 | 3/2008 | Daniel et al. |
| 7,344,533 B2 | 3/2008 | Pearson et al. |
| RE40,279 E | 4/2008 | Sluijter et al. |
| 7,364,578 B2 | 4/2008 | Francischelli et al. |
| 7,364,579 B2 | 4/2008 | Mulier et al. |
| 7,367,974 B2 | 5/2008 | Haemmerich et al. |
| 7,367,975 B2 | 5/2008 | Malecki et al. |
| 7,387,625 B2 | 6/2008 | Hovda et al. |
| D576,932 S | 9/2008 | Strehler |
| 7,419,486 B2 | 9/2008 | Kampa |
| 7,419,487 B2 | 9/2008 | Johnson et al. |
| 7,419,488 B2 | 9/2008 | Ciarrocca et al. |
| 7,419,489 B2 | 9/2008 | Vanney et al. |
| 7,422,586 B2 | 9/2008 | Morris et al. |
| 7,422,587 B2 | 9/2008 | Bek et al. |
| D594,736 S | 6/2009 | Esjunin |
| D594,737 S | 6/2009 | Kelly et al. |
| 7,553,309 B2 | 6/2009 | Buysse et al. |
| D606,203 S | 12/2009 | Husheer et al. |
| D613,412 S | 4/2010 | DeCarlo |
| 7,763,018 B2 | 7/2010 | DeCarlo et al. |
| 7,776,035 B2 | 8/2010 | Rick et al. |
| 7,811,283 B2 | 10/2010 | Moses et al. |
| 7,879,031 B2 | 2/2011 | Peterson |
| 7,885,625 B2 | 2/2011 | Muhammad et al. |
| D634,010 S | 3/2011 | DeCarlo |
| 8,034,052 B2 | 10/2011 | Podhajsky |
| 8,182,477 B2 | 5/2012 | Orszulak et al. |
| 8,211,099 B2 | 7/2012 | Buysse et al. |
| D681,810 S | 5/2013 | Decarlo |
| 8,568,402 B2 | 10/2013 | Buysse et al. |
| 2002/0111615 A1* | 8/2002 | Cosman et al. ............ 606/41 |
| 2002/0156472 A1 | 10/2002 | Lee et al. |
| 2003/0208193 A1* | 11/2003 | Van Wyk ............ 606/34 |
| 2005/0096681 A1 | 5/2005 | Desinger et al. |
| 2005/0155743 A1 | 7/2005 | Getz et al. |
| 2005/0192564 A1 | 9/2005 | Cosman et al. |
| 2006/0079886 A1* | 4/2006 | Orszulak et al. ............ 606/41 |
| 2006/0079887 A1* | 4/2006 | Buysse et al. ............ 606/41 |
| 2007/0066971 A1 | 3/2007 | Podhajsky |
| 2007/0073282 A1 | 3/2007 | McGaffigan et al. |
| 2007/0078453 A1 | 4/2007 | Johnson et al. |
| 2007/0078454 A1 | 4/2007 | McPherson |
| 2007/0100405 A1 | 5/2007 | Thompson et al. |
| 2008/0004615 A1 | 1/2008 | Woloszko et al. |
| 2008/0015664 A1 | 1/2008 | Podhajsky |
| 2008/0125775 A1 | 5/2008 | Morris |
| 2008/0147056 A1 | 6/2008 | van der Weide et al. |
| 2008/0183165 A1 | 7/2008 | Buysse et al. |
| 2011/0009804 A1 | 1/2011 | Behnke |
| 2011/0208177 A1 | 8/2011 | Brannan |
| 2011/0301589 A1 | 12/2011 | Podhajsky et al. |
| 2011/0301590 A1 | 12/2011 | Podhajsky et al. |
| 2011/0306969 A1 | 12/2011 | Coe et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 171967 A2 | 2/1986 |
| EP | 0 246 350 A1 | 11/1987 |
| EP | 310431 A2 | 4/1989 |
| EP | 0 521 264 A2 | 1/1993 |
| EP | 0 556 705 A1 | 8/1993 |
| EP | 0 558 429 A1 | 9/1993 |
| EP | 608609 A2 | 8/1994 |
| EP | 0 648 515 A1 | 4/1995 |
| EP | 0 836 868 A2 | 4/1998 |
| EP | 0 882 955 A1 | 12/1998 |
| EP | 1 070 518 A2 | 1/2001 |
| EP | 1 159 926 A2 | 12/2001 |
| EP | 1462065 A2 | 9/2004 |
| EP | 1465037 A2 | 10/2004 |
| EP | 1 645 234 A1 | 4/2006 |
| EP | 1656900 A2 | 5/2006 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |

(56) References Cited

FOREIGN PATENT DOCUMENTS

| | | |
|---|---|---|
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| KR | 20070093068 | 9/2007 |
| KR | 20100014406 | 2/2010 |
| KR | 20120055063 | 5/2012 |
| SU | 166452 | 11/1964 |
| SU | 401367 A1 | 10/1973 |
| SU | 727201 A2 | 4/1980 |
| WO | 93/24066 A1 | 12/1993 |
| WO | 94/28809 A1 | 12/1994 |
| WO | 96/04860 A1 | 2/1996 |
| WO | 96/18349 A2 | 6/1996 |
| WO | 96/29946 A1 | 10/1996 |
| WO | 96/34571 A1 | 11/1996 |
| WO | 96/39914 A1 | 12/1996 |
| WO | 97/06739 A2 | 2/1997 |
| WO | 97/06740 A2 | 2/1997 |
| WO | 97/06855 A2 | 2/1997 |
| WO | 97/17029 A1 | 5/1997 |
| WO | 9901074 A1 | 1/1999 |
| WO | 9904710 A1 | 2/1999 |
| WO | 9922657 A1 | 5/1999 |
| WO | 00/36985 A2 | 6/2000 |
| WO | WO00/36985 | 6/2000 |
| WO | 0067846 A1 | 11/2000 |
| WO | 0100114 A1 | 1/2001 |
| WO | 2004/045436 A1 | 6/2004 |
| WO | 2005009528 A1 | 2/2005 |
| WO | 2010/035831 A1 | 4/2010 |
| WO | WO2010/035831 | 4/2010 |

OTHER PUBLICATIONS

Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences. cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochennotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 pages, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.—Medical Professionals: Targis.TM. Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.

(56) References Cited

OTHER PUBLICATIONS

European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 12000334.8 dated May 4, 2012.
European Search Report EP 12000335.5 dated May 10, 2012.
European Search Report EP 12000336.3 dated May 14, 2012.
European Search Report EP 12001841.1 dated Jul. 16, 2012.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 1n Biologic Effects of Nonionizing Electromagnetic Fields, CRC Press, Inc., pp. 1424-1428.

Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw.cndot.Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15; (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Humphries Jr. et al., "Finite.cndot.Element Codes to Model Electrical Heating and Non.cndot.Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.

(56) References Cited

OTHER PUBLICATIONS

Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, filed May 2, 2013, Bahney.
U.S. Appl. No. 13/889,989, filed May 8, 2013, Lee.
U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.
U.S. Appl. No. 13/957,087, filed Aug. 1, 2013, Brannan.
U.S. Appl. No. 13/973,543, filed Aug. 22, 2013, Orszulak.
U.S. Appl. No. 14/011,414, filed Aug. 27, 2013, Ohri.
U.S. Appl. No. 14/011,438, filed Aug. 27, 2013, Ohri.
U.S. Appl. No. 14/014,937, filed Aug. 30, 2013, Willyard.
U.S. Appl. No. 14/017,995, filed Sep. 4, 2013, Brannan.
U.S. Appl. No. 14/018,081, filed Sep. 4, 2013, Brannan.

European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Oct. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009392.1 extended dated Sep. 19, 2011.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11000669.9 extended dated Jun. 30, 2011.
European Search Report EP 11001596.3 extended dated Jul. 4, 2011.
European Search Report EP 11001872.8 extended dated Jul. 6, 2011.
European Search Report EP 11004942 dated Oct. 4, 2011.
European Search Report EP 11009036.2 dated Feb. 13, 2012.
European Search Report EP 11010024.5 dated Apr. 20, 2012.
European Search Report EP 11010046.8 dated Apr. 17, 2012.

(56) References Cited

OTHER PUBLICATIONS

European Search Report EP 11010093.0 dated Mar. 27, 2012.
European Search Report EP 11010175.5 dated May 10, 2012.
European Search Report EP 11010176.3 dated Apr. 2, 2012.
European Search Report EP 11010177.1 dated May 10, 2012.
European Search Report EP 11174318.3 dated Nov. 7, 2011.
European Search Report EP 11185926.0 dated Feb. 3, 2012.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
US. Appl. No. 08/136,098, filed Oct. 14, 1993, Roger A. Stern.
U.S. Appl. No. 08/483,742, filed Jun. 7, 1995, Roger A. Stern.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,753, filed Jan. 6, 2012, Lee et al.
U.S. Appl. No. 13/344,790, filed Jan. 6, 2012, Lee et al.
U.S. Appl. No. 13/400,223, filed Feb. 20, 2012, Anthony B. Ross.
U.S. Appl. No. 13/477,307, filed May 22, 2012, Casey M. Ladtkow.
U.S. Appl. No. 13/483,858, filed May 30, 2012, Francesca Rossetto.
U.S. Appl. No. 13/488,964, filed Jun. 5, 2012, Steven P. Buysse.
U.S. Appl. No. 13/525,853, filed Jun. 18, 2012, Joseph A. Paulus.
U.S. Appl. No. 13/526,676, filed Jun. 19, 2012, Francesca Rossetto.
U.S. Appl. No. 13/539,650, filed Jul. 2, 2012, Joseph A. Paulus.
U.S. Appl. No. 13/539,690, filed Jul. 2, 2012, Steven P. Buysse.
U.S. Appl. No. 13/539,725, filed Jul. 2, 2012, Steven P. Buysse.
U.S. Appl. No. 13/539,875, filed Jul. 2, 2012, Mani N. Prakash.
U.S. Appl. No. 13/551,005, filed Jul. 17, 2012, Chris Rusin.
U.S. Appl. No. 13/567,624, filed Aug. 6, 2012, Mani N. Prakash.
U.S. Appl. No. 13/568,679, filed Aug. 7, 2012, Robert J. Behnke, II.
U.S. Appl. No. 13/596,785, filed Aug. 28, 2012, Richard A. Willyard.
U.S. Appl. No. 13/598,141, filed Aug. 29, 2012, Kenlyn S. Bonn.

(56) References Cited

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

Anderson et al., "A Numerical Study of Rapid Heating for High Temperature Radio Frequency Hyperthermia" International Journal of Bio-Medical Computing, 35 (1994), pp. 297-307.

Anonymous. (1999) Auto Suture MIBB Site Marker: Single Use Clip Applier, United States Surgical (Product instructions), 2 pages.

Anonymous. (2001) Disposable Chiba Biopsy Needles and Trays, Biopsy and Special Purpose Needles Cook Diagnostic and Interventional Products Catalog (products list), 4 pages.

Anonymous. (1987) Homer Mammalok.TM. Breast Lesion Needle/Wire Localizer, Namic.RTM. Angiographic Systems Division, Glens Falls, New York, (Hospital products price list), 4 pages.

Anonymous. (1999) MIBB Site Marker, United States Surgical (Sales brochure), 4 pages.

Anonymous. Blunt Tubes with Finished Ends. Pointed Cannula, Popper & Sons Biomedical Instrument Division, (Products Price List), one page, Jul. 19, 2000.

Anonymous. Ground Cannulae, ISPG, New Milford, CT, (Advertisement) one page, Jul. 19, 2000.

B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.

B. Levy M.D. et al., "Update on Hysterectomy New Technologies and Techniques" OBG Management, Feb. 2003.

B. Levy M.D., "Use of a New Vessel Ligation Device During Vaginal Hysterectomy" FIGO 2000, Washington, D.C.

\* cited by examiner

THERMAL FEEDBACK SYSTEMS AND METHODS OF USING THE SAME

CROSS-REFERENCE TO RELATED APPLICATIONS

The present application is a continuation application of U.S. patent application Ser. No. 13/539,725, now U.S. Pat. No. 8,568,402, filed Jul. 2, 2012, which is a divisional application of U.S. patent application Ser. No. 12/023,606, now U.S. Pat. No. 8,211,099, filed Jan. 31, 2008, which claims the benefit of and priority to U.S. Provisional Application Ser. No. 60/887,537, filed on Jan. 31, 2007, the entire contents of all of which are incorporated by reference herein.

BACKGROUND

1. Technical Field

The present disclosure relates to energy delivery feedback systems and, more particularly to thermal feedback systems for electrosurgical energy systems and methods of their use.

2. Background of Related Art

The use of electrical energy including radiofrequency and microwave energy ("RF & MW energy") and, in particular, radiofrequency electrodes or microwave antennae ("RF-electrodes/MW-antennae") for ablation of tissue in the body or for the treatment of pain is known. Generally, such RF electrodes (e.g., probes, resistive heating elements and the like) include an elongated cylindrical configuration for insertion into the body to target tissue which is to be treated or ablated. The RF electrodes can further include an exposed conductive tip portion and an insulated portion. The RF electrodes can also include a method of internal cooling (e.g., a Cool-tip™ or the like), such as the RF electrodes shown and described in U.S. Pat. No. 6,506,189 entitled "COOL-TIP ELECTRODE THERMOSURGERY SYSTEM" issued to Rittman, III et al., on Jan. 14, 2003 and U.S. Pat. No. 6,530,922 entitled "CLUSTER ABLATION ELECTRODE SYSTEM" issued to Cosman et al., on Mar. 11, 2003, the entire content of which is incorporated herein by reference. Accordingly, when the RF electrode is connected to an external source of radiofrequency power, e.g., an electrosurgical generator (device used to generate therapeutic energy such as radiofrequency (RF), microwave (MW) or ultrasonic (US)), and current is delivered to the RF electrode, heating of tissue occurs near and around the exposed conductive tip portion thereof, whereby therapeutic changes in the target tissue, near the conductive tip, are created by the elevation of temperature of the tissue.

In some applications, for example, tumor ablation procedures, multiple electrodes are inserted into the body in an array to enlarge ablation volumes.

In a particular application, arrays of high frequency electrodes are inserted into tumors. The electrodes are typically placed in a dispersed fashion throughout the tumor volume to cover the tumor volume with uniform heat. The multiple electrodes may be activated simultaneously or sequentially applied with high frequency energy so that each electrode heats the surrounding tissue. During series activation, energy is applied to each electrode one at a time. This sequence of cycling the energy through the electrodes continues at a prescribed frequency and for a period of time.

The electrode systems discussed above are limited by the practical size of lesion volumes they produce. Accordingly, electrodes with cooled conductive tips have been proposed. With cooling, radiofrequency electrode tips generally produce larger lesion volumes compared with radiofrequency electrodes, which are not cooled. For example, standard single cylindrical electrodes, with cooled tips, as described above, may make lesion volumes up to 2 to 3 cm in diameter in living tissue (e.g., the liver) by using needles of 1 to 2 mm in diameter and having exposed tip lengths of several centimeters.

SUMMARY

The present disclosure relates to thermal feedback systems for electrosurgical energy systems and methods of their use.

According to an aspect of the present disclosure, a system for providing feedback during an electrosurgical procedure on a target tissue is provided. The system includes an electrosurgical energy source; an electrode probe assembly connected to the electrosurgical energy source, wherein the electrode probe assembly includes at least one electrode assembly having a needle configured to deliver electrosurgical energy to the target tissue; at least one thermal feedback assembly connected to the electrosurgical energy source, wherein each thermal feedback assembly includes at least one temperature sensor assembly; and a hub configured to selectively support the electrode probe assembly and each thermal feedback assembly such that the needle of the electrode probe assembly and each temperature sensor assembly of each thermal feedback assembly are proximate one another when disposed proximate the target tissue.

The needle of the electrode probe assembly may include an electrically conductive distal tip electrically connected to the electrosurgical energy source.

The electrode probe assembly may be fluidly connected to a coolant supply and may be configured to receive a circulating fluid therein.

The thermal feedback assembly may include a one or more temperature sensors. Each temperature sensor may be oriented substantially parallel to an axis defined by the needle of the electrode probe assembly or protrude 90 degrees from the center exposed active electrode. The plurality of temperature sensors may be arranged in a linear array. The plurality of temperature sensors may be disposed on opposed sides of the needle of the electrode probe assembly. The plurality of temperature sensors may be uniformly spaced from one another. The plurality of temperature sensors may be arranged in one of a linear, rectilinear and a triangular array.

The system may further include a computer connected to at least one of the electrosurgical energy source, the electrode probe assembly and each thermal feedback assembly. In an embodiment, at least one of the electrosurgical or microwave generator, the electrode probe assembly and each thermal feedback assembly may transmit information to the computer, and wherein the computer performs an Arrhenius model calculation on the information received from the at least one of the electrosurgical energy source, the electrode probe assembly and each thermal feedback assembly.

The temperature sensors may include fiber optic temperature probes, thermisters, thermocouples or resistive temperature devices (RTD).

According to another aspect of the present disclosure, a method of performing a thermal treatment on a target tissue is provided. The method comprises the steps of providing an electrosurgical energy source; and providing a thermal feedback system. The thermal feedback system includes an electrode probe assembly connectable to the electrosurgical generator, wherein the electrode probe assembly includes at least one electrode assembly having a needle configured to deliver electrosurgical energy to the target tissue; at least one thermal feedback assembly connectable to the electrosurgical energy source, wherein each thermal feedback assembly includes at least one temperature sensor assembly; and a hub configured to selectively support the electrode probe assembly and each thermal feedback assembly such that the needle of the electrode probe assembly and each temperature sensor assembly of each thermal feedback assembly are proximate one another when disposed proximate the target tissue.

The method further includes the steps of inserting the needle of the electrode probe assembly and each temperature sensor of the thermal feedback assembly into a patient proximate the target tissue; activating the electrosurgical energy source for delivering electrosurgical energy to the target tissue via the needle of the electrode probe; and monitoring and transmitting changes in a characteristic of the target tissue to the electrosurgical energy source via the temperature sensors of the thermal feedback assembly.

The method may further include the step of performing an Arrhenius model calculation on the information received from each thermal feedback assembly.

The method may further include the step of selecting a particular electrode probe assembly for a particular thermal procedure or desired treatment size or volume. Size estimation may be accomplished prior to delivery of the electrode probe assembly. The method may further include the step of selecting a characteristic energy value to be delivered to the particular electrode probe assembly based on the characteristics of the electrode probe assembly and the characteristics of the target tissue to be treated.

The method may further include the step of providing feedback to the electrosurgical energy source from the plurality of thermal feedback probes. Size estimation may be conducted during energy activation.

The method may further include the step of providing a computer configured to receive information regarding characteristics of at least one of the target tissue, the feedback of energy delivery, the electrode probe assembly, the thermal feedback assembly and the electrosurgical energy source. The computer may be configured to receive feedback information from the thermal feedback assembly during a thermal treatment of the target tissue. The computer may be configured to perform an Arrhenius model calculation or other ablation size estimation on the information received from each thermal feedback assembly.

The method may further include the step of arranging the electrode probe assembly and each thermal feedback assembly in a linear array.

The method may further include the step of spacing the thermal feedback assemblies equally from each other and from the electrode probe assembly.

The method may further include the step of spacing the thermal feedback assemblies at a known or predetermined spacing.

The method may further include the step of circulating a fluid through the electrode probe assembly.

The method may further include the step of introducing the electrode probe assembly and each of the plurality of thermal feedback assemblies into the target tissue.

These and other aspects and advantages of the disclosure will become apparent from the following detailed description and the accompanying drawings, which illustrate by way of example the features of the disclosure.

BRIEF DESCRIPTION OF THE DRAWINGS

The features of the system and method of use of the system of the present disclosure will become more readily apparent and may be better understood by referring to the following detailed descriptions of illustrative embodiments of the present disclosure, taken in conjunction with the accompanying drawings, wherein.

DETAILED DESCRIPTION OF EMBODIMENTS

Figure 1:
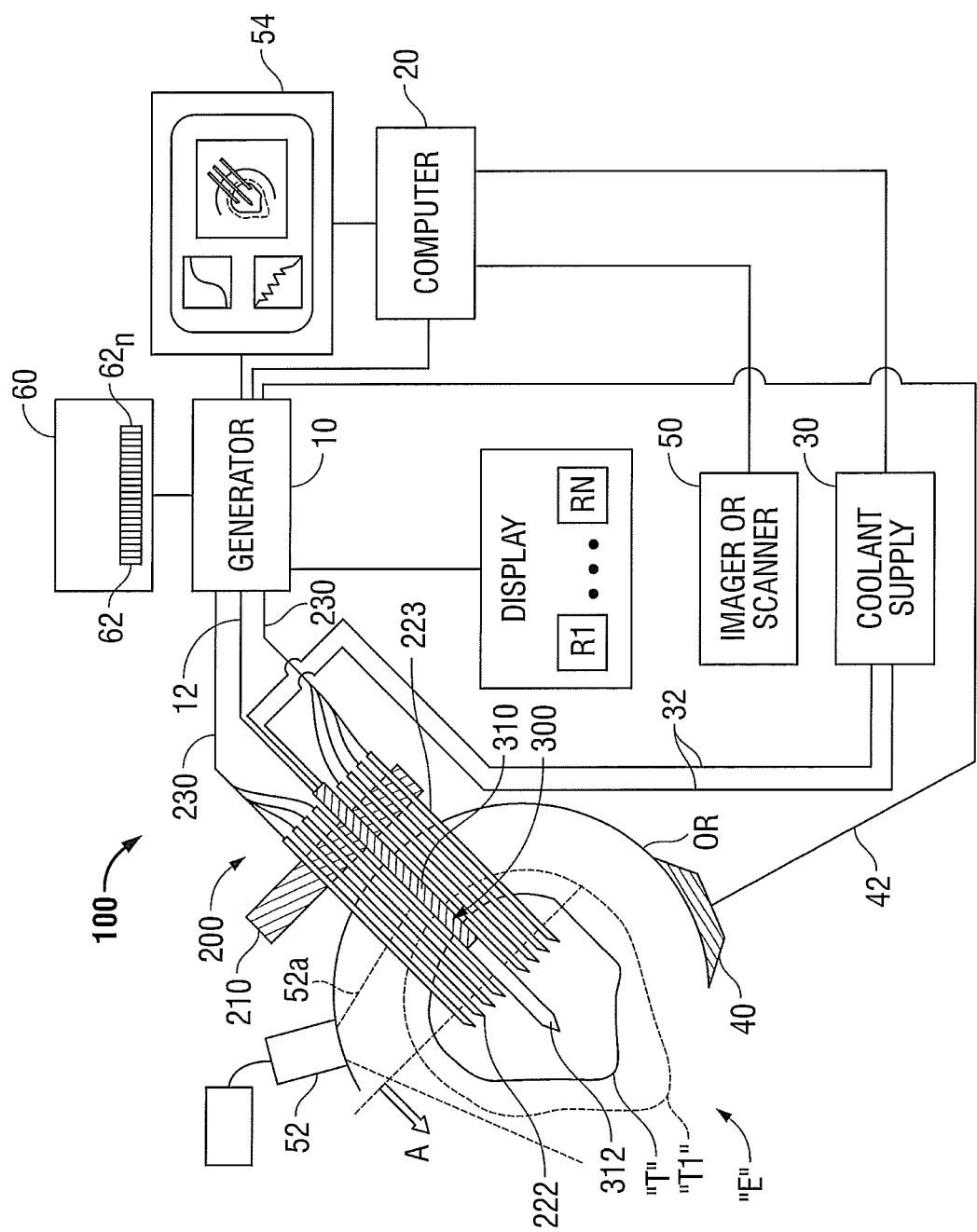
FIG. 1 is a schematic illustration of a thermal feedback system illustrating an electrode probe assembly and a thermal feedback assembly of the present disclosure operatively associated with a target surgical site.

The systems and methods of the present disclosure provide for a more precise controlled monitoring and/or feedback of an electrode probe during therapeutic use in a target surgical site, e.g., in a cancer tumor. Moreover, the systems and methods of the present disclosure provide for an improved ability to predict and/or estimate the depth and/or volume of treatment possible by the electrode probe when the electrode probe of an electrosurgical treatment device is set to a particular or various operative parameters.

It will be readily apparent to a person skilled in the art that the systems and methods of use of the systems can be used to monitor or provide feedback during treatment of body tissues in any body cavity or tissue locations that are accessible by percutaneous or endoscopic catheters or open surgical techniques, and is not limited to cancer tumors or the like. Application of the systems and methods in any corporal organ and/or tissue is intended to be included within the scope of the present disclosure.

1. System for Thermal Feedback

In the drawings and in the description which follows, the term "proximal", as is traditional, will refer to the end of the system, or component thereof, which is closest to the operator, and the term "distal" will refer to the end of the system, or component thereof, which is more remote from the operator.

With reference to FIG. 1, a thermal feedback system, according to an embodiment of the present disclosure, is generally designated as 100. Feedback system 100 includes a thermal feedback assembly 200 operatively connected to an electrosurgical generator and/or energy source 10 and/or computer 20.

At least one electrode probe assembly 300 is provided which is operatively associated with feedback assembly 200 and is connectable to electrosurgical energy source 10 in order to perform tissue ablation and the like. Each electrode probe assembly 300 may include a rigid shaft, antenna or needle 310 configured for insertion into a target tissue or organ "OR". Needle 310 of each probe assembly 300 may terminate in an exposed distal tip 312 having a pointed configuration for facilitating percutaneous insertion of needle 310 into body organ "OR". A portion of the external surface of needle 310 of each electrode probe assembly 300 is covered with an insulating material, as indicated by hatched line areas in FIG. 1. Distal tip 312 remains uncovered and is connected, through needle 310, to cable 12 and thereby to electrosurgical energy source 10. Electrode probe assembly 300 may include a coolant supply 30 fluidly connected to needle 310 for circulating a fluid thereto via conduit(s) 32.

Reference may be made to commonly assigned U.S. application Ser. No. 11/495,033, filed on Jul. 28, 2006, and entitled "COOL-TIP THERMOCOUPLE INCLUDING TWO-PIECE HUB" for a detailed discussion of the construction and operation of electrode probe assembly 300.

Temperatures at, or near the exposed distal tip(s) 312 of needle(s) 310 may be controlled by adjusting a flow of fluid coolant through needle 310. Accordingly, the temperature of the tissue contacting at or near distal tip(s) 312 is controlled. In operation, fluid from coolant supply 30 is carried the length of needle 310 through an inner tube (not shown) extending therethrough to the distal end of needle 310 terminating in an open end or cavity (not shown) of distal tip 312. At the opposite end of needle 310, the inner tube is connected to receive fluid. Backflow from distal tip(s) 312 is through an exit port (not shown) of needle 310.

Feedback system 100 may further include a reference electrode 40 that may be placed in contact with the skin of a patient or an external surface of organ "OR" with a connection 42 to electrosurgical energy source 10. Reference electrode 40 and connection 42 serve as a path for return current from electrosurgical energy source 10 through needle 310 of electrode probe assembly 300.

As seen in FIG. 1, by way of illustration only, a targeted region to be ablated is represented in sectional view by the line "T". It is desired to ablate the targeted region "T" by fully engulfing targeted region "T" in a volume of lethal heat elevation. The targeted region "T" may be, for example, a tumor which has been detected by an image scanner 50. For example, CT, MRI, fluoroscopy or ultrasonic image scanners may be used, and the image data transferred to computer 20. As an alternate example, an ultrasonic scanner head 52 may be disposed in contact with organ "OR" to provide an image illustrated by lines 52a.

For example, in FIG. 1, dashed line "T1" represents the ablation isotherm in a sectional view through organ "OR". Such an ablation isotherm may be that of the surface achieving possible temperatures of approximately 50° C. or greater. At that temperature range, sustained for approximately 30 seconds to approximately several minutes, tissue cells will be ablated. The shape and size of the ablation volume, as illustrated by dashed line "T1", may accordingly be controlled by a configuration of the electrode probe assemblies 300 used, the geometry of distal tips 312 of electrode probe assemblies 300, the amount of RF power applied, the time duration that the power is applied, the cooling of the needles 310 of electrode probe assemblies 300, etc.

Data processors may be connected to display devices to visualize targeted region "T" and/or ablation volume "T1" in real time during the ablation procedure.

As seen in FIG. 1, feedback system 100 may further include a library 60 including a plurality of thermal profiles/overlays $62_n$. As used herein, the term library is understood to include and is not limited to repository, databank, database, cache, storage unit and the like. Each overlay 62 includes a thermal profile which is characteristic of and/or specific to a particular configuration of cannula/electrode assembly or amount of exposure (i.e., specific to the length of exposure of distal tip 312 of needle 310 or the amount of needle 310 extending from a distal tip of a cannula) of the cannula/electrode assembly. In addition, for each amount of exposure or configuration of the cannula/electrode assembly, a plurality of overlays $62_n$ is provided which includes a thermal profile which relates to, for example, the amount of time electrode probe assembly 300 is activated, to the temperature to which electrode probe assembly 300 is heated, etc.

With continued reference to FIG. 1, feedback system 100, as mentioned above, includes a thermal feedback assembly 200 operatively connected to an electrosurgical generator 10 and/or computer 20. Thermal feedback assembly 200 is operatively associated with the at least one electrode probe assembly 300.

As seen in FIG. 1, feedback assembly 200 includes a hub or housing 210 configured to selectively support at least one electrode probe assembly 300 and at least one temperature sensor assembly 220. As seen in FIG. 1, a plurality of temperature sensor assemblies 220 are shown supported in housing 210 on opposed sides of a single electrode probe assembly 300. It is contemplated that any number of temperature sensor assemblies 220 may be disposed on a single side, on opposed sides, or on multiple sides of the single electrode probe assembly 300 or relative to multiple electrode probe assemblies 300. It is further contemplated that multiple temperature sensor assemblies 220 may be interspersed amongst multiple electrode probe assemblies 300. Individual needles, cannula or introducers 223 may be used to introduce temperature sensors 222 into the target site or organ "OR".

Figure 2:
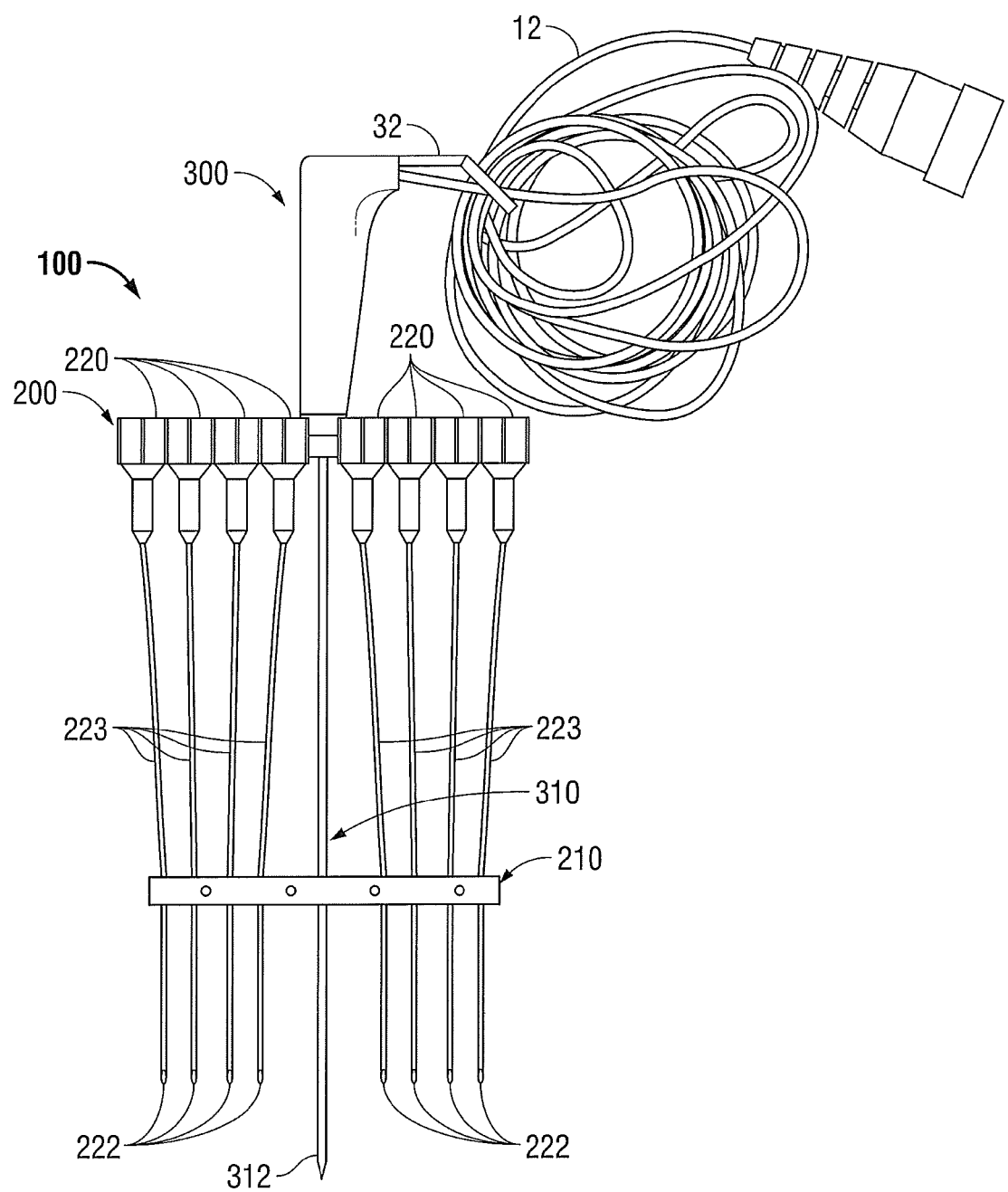
FIG. 2 is an illustration of the thermal feedback system of FIG. 1.

As seen in FIG. 2, housing 210 is used to position temperature sensor assemblies 220 on opposed sides of a singe electrode probe assembly 300 so as to define a single axis or plane. Housing 210 may be configured to position cannula 223 and temperature sensors 222 of temperature sensor assemblies 220 at a known distance from electrode probe assembly 300 and/or from one another, or are equi-distant or uniformly spaced from one another.

Figure 2A:
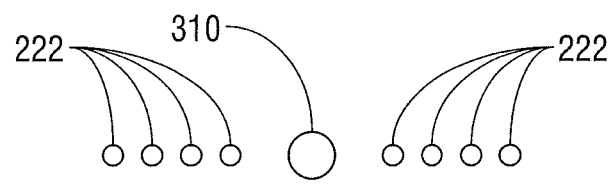
FIG. 2A is a schematic distal end view of the thermal feedback system of FIG. 2, illustrating the temperature array in a linear arrangement.
Figure 2B:
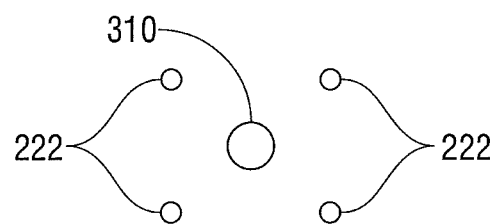
FIG. 2B is a schematic distal end view of an alternate arrangement of the thermal feedback system of FIG. 2, illustrating the temperature array in a rectangular arrangement.
Figure 2C:
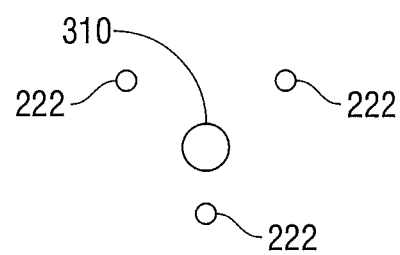
FIG. 2C is a schematic distal end view of a further alternate arrangement of the thermal feedback system of FIG. 2, illustrating the temperature array in a triangular arrangement.
Figure 2D:
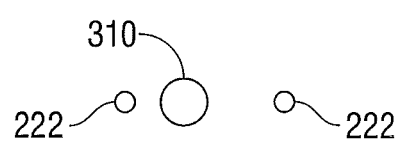
FIG. 2D is a schematic distal end view of the thermal feedback system of FIG. 2, illustrating the temperature array in an alternate linear arrangement.
Figure 3:
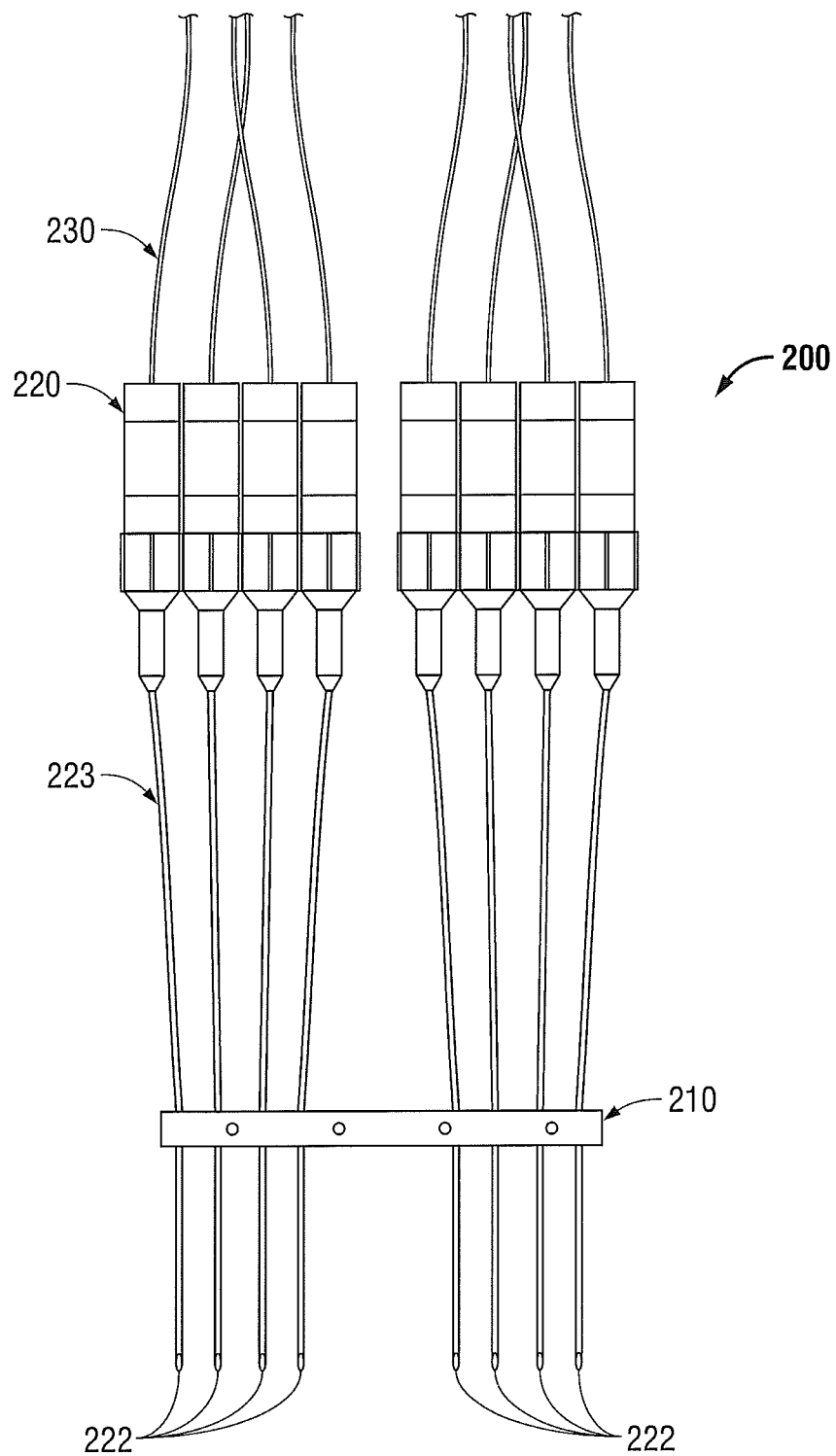
FIG. 3 is an illustration of a feedback/monitoring assembly of the thermal feedback system.
Figure 4:
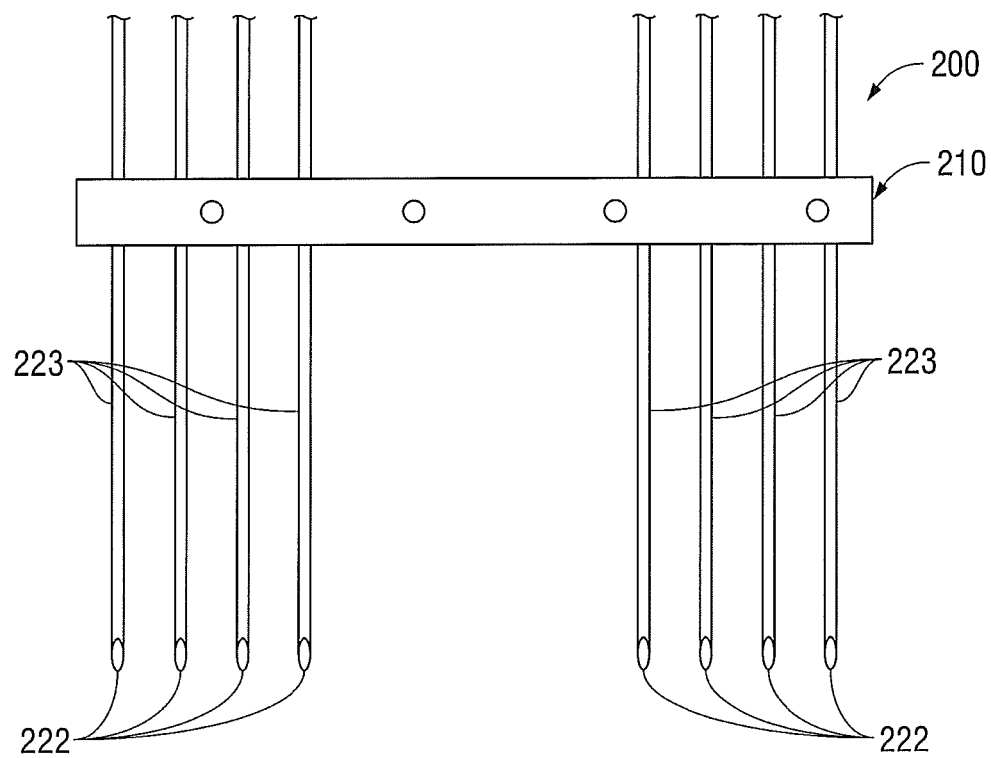
FIG. 4 is an enlarged view of the indicated area of detail of FIG. 3.

As seen in FIG. 2A, temperature sensors 222 and electrode assembly 310 are arranged in a linear array. As seen in FIG. 2B, temperature sensors 222 and electrode assembly 310 may be arranged in a rectilinear array. As seen in FIG. 2C, temperature sensors 222 and electrode assembly 310 may be arranged in a triangular array. As seen in FIG. 2D, temperature sensors 222 are arranged at a known distance from electrode assembly 310. As seen in FIGS. 2-2D, electrode assembly 310 is located at the center of temperature sensors 222; however, electrode assembly 310 may be located at any position relative to sensors 222.

Each temperature sensor assembly 220 is electrically or optically connected to electrosurgical generator 10 via a suitable electrical connector or the like 230.

Temperature sensors 222 include one or more of an emitter, sensor or marker to provide special relationship to electrode assembly 310. Each temperature sensor assembly 220 may include a temperature sensor 222 in the form of a rigid or semi-rigid cannula 223 and/or needles configured for insertion and/or penetration into the target surgical site. Suitable temperature sensors 222 may include thermocouples, resistive temperature devices (RTD) or fiber optic temperature probes sold under the tradename "Fluoroptic® Thermometer, available from Luxtron®, Santa Clara, Calif. Temperature sensors 222 are shown and described in U.S. Pat. Nos. 4,075, 497; 4,215,275; 4,448,547; 4,560,286; 4,752,141; 4,883,354; and 4,988,212.

Fluoroptic® temperature sensors 222 are configured to measure the decay time of light emitted from phosphorescent materials (e.g., phosphors). The decay time is a persistent property of the sensor that varies directly with the temperature.

Other suitable temperature sensors for use with temperature sensor assemblies 220, to measure the temperature at a target surgical site, include and are not limited to optical sensors (e.g., Flouroptic®, infrared, etc.), thermocouples, Resistance-Temperature-Detectors (RTD), thermistors, MRI, fluoroscopic, ultrasound, CT and the like.

Temperature sensors 222 may be configured to measure or monitor temperatures greater than about 60° C. In an embodiment, feedback system 100 may be provided with suitable algorithms or the like for interpolating temperature values from at least two temperature sensors 222 and/or for integrating thermal damage from at least two temperature sensors 222. One real-time temperature sensor may be used in conjunction with an assumed or predetermined value from a look-up table or similar method.

The temperature measurements delivered to feedback system 100 may be used to generate a thermal map of the target area and/or, upon integration, may be used to account for particular tissue characteristics, such as, for example, perfusion, conduction, resistance and/or density.

Figure 7A:
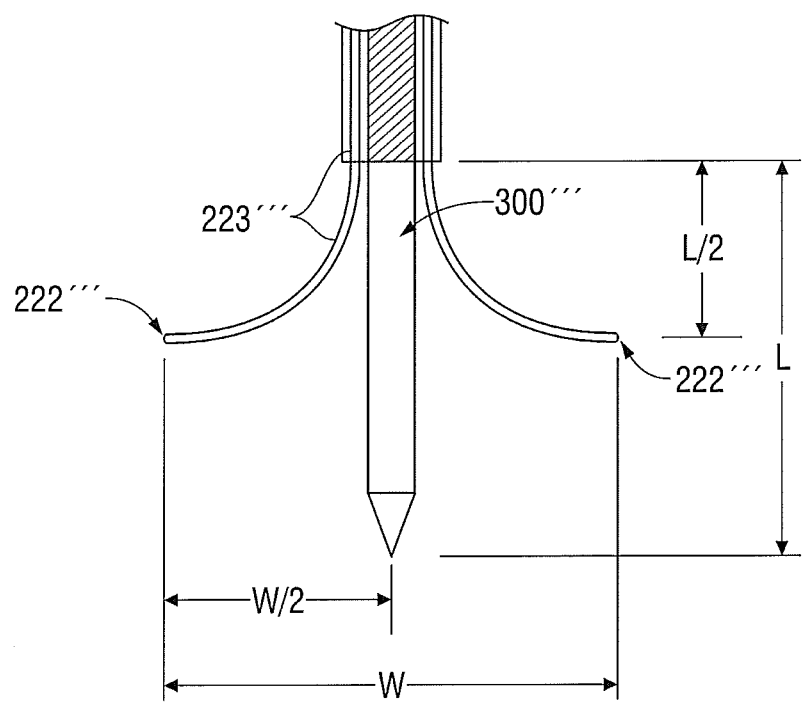
FIG. 7A is a schematic illustration of a distal end of an electrode probe according to an embodiment of the present disclosure.
Figure 7B:
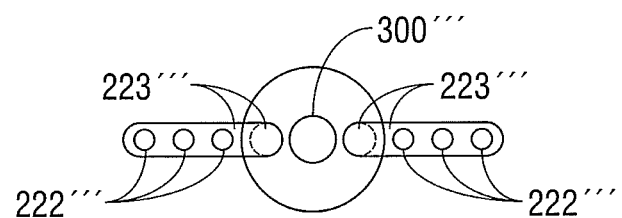
FIG. 7B is a distal, elevational view of the electrode probe of FIG. 7A.

In an embodiment, temperature sensors 222 may be deployed around needle 310 of the electrode probe assembly 300. Such temperature sensors may be constructed of suitable shape memory alloys so as to permit the temperature sensor to wrap around needle 310. Additionally, in an embodiment, a cannula including temperature sensors may be deployed about needle 310 of the electrode probe assembly 300. In another embodiment, as seen in FIGS. 7A and 7B, temperature sensors 222 may protrude at a substantially right angle from a center or mid point of the exposed distal tip 312 of needle 310.

Electrosurgical generator 10 and electrode probe assembly 300 may be configured to deliver energy to at least one of a radiofrequency, a microwave, an ultrasound, and a cryotherapy needle.

Feedback system 100 is capable of providing size predictability for ablation volume to be created during a thermal procedure of a target region prior to the ablation volume exceeding a predetermined volume during the thermal procedure. For example, feedback system 100 may provide feedback regarding a volume of the thermal therapy (e.g., diameter), and estimation of an overall size of the volume of the thermal therapy, an estimation of a rate of growth of the volume of the thermal therapy, and/or an estimation of a time to completion of the thermal therapy. All of this information may be displayed on a monitor 54 (See FIG. 1) or the like. Additionally, monitor 54 may illustrate the growth of the ablation volume, in real-time, as the procedure is going forward.

Figure 5:
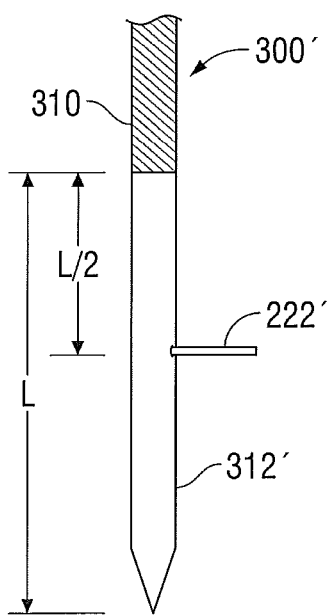
FIG. 5 is a schematic illustration of a distal end of an electrode probe assembly according to a further embodiment of the present disclosure.
Figure 6:
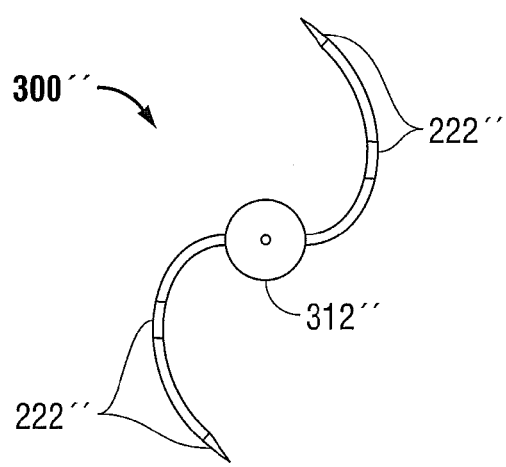
FIG. 6 is a distal end view of an electrode probe assembly similar to the electrode probe assembly of FIG. 5.

As seen in FIGS. 5-7, a distal end of electrode probe assemblies according to further embodiments of the present disclosure are generally designated as 300' and 300", respectively. Electrode probe assembly 300', 300''' is substantially similar to electrode probe assembly 300 and thus will only be discussed in further detail herein to the extent necessary to identify differences in construction and operation thereof.

As seen in FIGS. 5 and 7, distal tip 312' of electrode probe assembly 300' has a length of exposure "L". Additionally, electrode probe assembly 300' is configured such that temperature sensor 222' extends radially outward therefrom at a location approximately equal to "L/2". As seen in FIG. 5, temperature sensor 222' may extend radially and linearly from electrode probe assembly 300' (e.g., in a plane that is substantially orthogonal to a longitudinal axis of electrode probe assembly 300'), or, as seen in FIG. 6, temperature sensor 222" may extend radially and arcuately from electrode assembly 300" (e.g., in a plane that is substantially orthogonal to a longitudinal axis of electrode probe assembly 300").

As seen in FIG. 5, a single temperature sensor 222' may extend from electrode assembly 300', and as seen in FIG. 6, a pair of temperature sensors 222" may extend from electrode assembly 300". In any of the embodiments disclosed herein, any number of temperature sensors 222' or 222" may be used to extend from electrode assembly 300', 300" or 300'.

Each temperature sensor 222' or 222" may include at least one, and as seen in FIGS. 5 and 6, a plurality of discrete respective temperature sensor elements $222a'$, $222a''$ disposed along a length thereof, such as, for example, at least at a tip thereof, at a mid-point thereof and at a base or proximal end thereof.

As seen in FIGS. 5 and 6, each temperature sensor 222' or 222" may be slidably disposed within a respective electrode probe assembly 300', 300" and configured so as to project and/or retract from within electrode probe assembly 300' or 300". Each temperature sensor 222', 222" may extend along an outer surface of a respective electrode probe assembly 300', 300".

Each temperature sensor 222', 222" may be deployable to a known and/or predetermined radial distance from respective distal tips 312', 312" of respective electrode probe assembly 310', 310". In accordance with FIG. 6, or in embodiments employing multiple temperature sensors 222", the multiple temperature sensors 222" may be deployed to a known and/or predetermined distance from one another.

As seen in FIG. 7, temperature sensors 222''' may be disposed to a known and/or predetermined radial distance from electrode probe assembly 300'''. Temperature sensors 222''' are generally disposed L/2 and 1/2 desired diameter of thermal ablation (W/2), wherein "L" is the length of exposure of the distal end of electrode probe assembly 300''' and "W" is the approximate diameter of the thermal ablation.

2. Method for Thermal Feedback

With reference to FIGS. 1-7B, a method of using thermal feedback system 100 during the thermal treatment of a target tissue or organ "OR" with electrode probe assembly 300, 300' or 300", in conjunction with hyperthermia feedback assembly 200, is described.

A method of the present disclosure includes determining a zone of thermal treatment during and/or post treatment of the target tissue or organ "OR". The method may comprise the step of measuring a temperature of the target tissue or organ "OR", at known distances relative thereto, during and/or post treatment of the target tissue or organ "OR". The temperature of the target tissue or organ "OR", at the known distance, may be an absolute temperature and/or a temperature that is interpolated. Additionally, the method may comprise integrating the temperature over time to determine an extent of thermal treatment. Such an integration may be calculated using an "Arrhenius thermal treatment integral" or other methods of thermal damage estimation.

As used herein, "thermal damage" is a term that describes a quantity representing a relative amount of destruction to a tissue component. The component of interest can vary widely between applications from sub-cellular components, such as, for example, protein or organelles, to many celled systems, such as, for example, tumors or organs. To study systems spanning such a wide range of scale different techniques may be applied. For a relatively small system, one approach may be an "ab initio" method or some other molecular dynamic approach. For relatively larger systems, one approach may be to use an empirical method, such as, for example, the "Arrhenius" method described herein or a critical temperature criterion.

The term "Arrhenius thermal treatment" refers to a method of quantifying thermal effects on underlying tissue. The present method thus models microscopic effects in tissue, such as, for example, the denaturation of a single species of protein, or models macroscopic effects in tissue, such as, for example, a color change of the tissue associated with the thermal treatment where many different reactions have taken place.

The equation for the "Arrhenius model" may be represented by the following equation:

$$\Omega(t) = -\ln\left(\frac{c(t)}{c(o)}\right) = A \int_0^t e^{\left(\frac{-\Delta E}{RT}\right)} dt$$

where:

$\Omega$ = is the thermal effect sustained by the tissue or organ;

$c(t)$ = is the amount of the component of interest remaining;

$c(0)$ = is the amount of the component of interest at time zero;

A = is the frequency factor, approximately $7.39 \times 10^{39}$ 1/s (specific to liver tissue); and $\Delta E$ = is the activation energy, approximately $2.577 \times 10^5$ J/mol (specific to liver tissue).

The "Arrhenius model" is used because, in addition to combined processes, the "Arrhenius model" applies to individual processes as well. Individual processes that may be of interest include and are not limited to the denaturation of a lipid bi-layer of a cell, the denaturation of mitochondrial proteins, and the denaturation of nuclear proteins. The denaturation of lipid bi-layer is of interest because the lipid bi-layer loses its structure before many other parts of a cell. The denaturation of mitochondrial and nuclear proteins is of interest because they denature at temperatures in the range of about 42 to 60° C.

A method of the present disclosure may also include the step of using a position of electrode probe assembly 300, 300' or 300" and needle 310, positional temperature and/or feedback temperature received from hyperthermia feedback assembly 200 to determine the extent of thermal effect or treatment to the target tissue or organ "OR". The position of electrode probe assembly 300, 300' or 300" and needle 310 may be determined using a suitable positional indicator. The positional temperature may be determined by the location of temperature sensor 222, 222', 222" or 222''' and may be used to determine the presence of the lack of heat in the tissue or organ "OR".

A method of the present disclosure may also include the step of determining the spatial relationship between electrode probe assembly 300 and temperature sensor 222. Spatial relationship of electrode probe assembly 300 and temperature sensor 222 and temperature measured at temperature sensor 222 are feedback to computer 20 to determine an extent of thermal damage that may be displayed on monitor 54 or used to alter the output of electrosurgical energy source 10.

A method of the present disclosure may use a three-dimensional (3D) thermal image/map to determine a dimension of thermal treatment of the target tissue of organ "OR".

According to a method of the present disclosure, computer 20 of feedback system 100 is provided with information regarding a location of the target tissue or organ "OR", a location of critical biological structures (e.g., tissue, organs, vessels, etc.), a size and/or shape of the tumor or the target tissue or organ "OR" to be thermally treated, and a desired size of the thermal treatment volume. With this information inputted into computer 20, computer 20 may apply the "Arrhenius model" in order to develop a course of treatment.

According to a method of the present disclosure, an electrode probe assembly 300, 300' or 300" including a particular needle 310 having a given length "L" of exposure of distal tip 312 thereof is selected for a particular thermal procedure. A length "L" of electrode exposure may be user selected based on a desired volume of tissue to be treated or diameter "W" of thermal treatment. With the particular electrode probe assembly 300, 300' or 300" selected the parameters (e.g., dimensions, power rating, etc.) of electrode probe assembly 300, 300' or 300" is manually inputted or automatically selected from a look-up table for use by the electrosurgical generator 10 and/or computer 20.

With the parameters or characteristics of the tumor, target tissue or organ "OR" inputted into the electrosurgical energy source 10 and/or computer 20 and the parameters or characteristics of the electrode probe assembly 300, 300' or 300" selected also inputted into the electrosurgical generator 10 and/or computer 20, the parameters of the energy to be delivered to the tumor, target tissue or organ "OR", via the electrode probe assembly 300, 300' or 300", are determined. As seen in FIG. 1, with the parameters of the energy to be delivered determined, thermal feedback assembly 200 and with electrode probe assembly 300 inserted into the patient, proximate the tumor, target tissue or organ "OR". In particular, temperature sensors 222 of thermal feedback assembly 200 and needle 310 of electrode probe assembly 300 may be inserted into the tumor, target tissue or organ "OR".

With thermal feedback assembly 200 and electrode probe assembly 300 positioned, the placement of thermal feedback assembly 200 and electrode probe assembly 300 is confirmed. Next, a spatial relationship of temperature sensors 222 and electrode probe assembly 300 may be determined by using thermal feedback assembly 200 or use of other markers, and communicated to electrosurgical energy source 10 and/or computer 20 for use of feedback control of energy parameter and/or size estimation. After confirmation of the placement of thermal feedback assembly 200 and electrode probe assembly 300 the thermal treatment of the tumor, target tissue or organ "OR" may begin. The thermal treatment of the tumor, target tissue or organ "OR" includes delivering energy produced by electrosurgical generator 10 to the tumor, target tissue or organ "OR" via electrode probe assembly 300.

During the thermal treatment of the tumor, target tissue or organ "OR" hyperthermia feedback assembly 200 provides feedback to electrosurgical energy source 10 and/or computer 20 in the manner described above. Treatment progress is determined by computer 20 with feedback from at least one of image scanner 5, electrosurgical energy source 10, and temperature sensors 222. Treatment progress is displayed on monitor 54. Treatment progress includes one of size estimation, rate of treatment progression, and relationship of treatment volume to target volume.

While the above description contains many specific examples, these specific should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A method for treating tissue, comprising:
inserting an electrode probe assembly and at least one thermal feedback assembly into tissue, the electrode probe assembly and the at least one thermal feedback assembly being disposed in a hub;
activating an electrosurgical generator coupled to the electrode probe assembly and the at least one thermal feedback assembly to deliver electrosurgical energy to the tissue through the electrode probe assembly to thermally treat the tissue;
measuring a temperature of the tissue at the at least one thermal feedback assembly; and
transmitting the measured temperature to the electrosurgical generator.

2. The method according to claim 1, further comprising:
controlling delivery of the electrosurgical energy based on the measured temperature.

3. The method for treating tissue according to claim 1, further comprising:
estimating a desired thermal treatment volume in response to thermal treatment of the tissue based on the measured temperature.

4. The method for treating tissue according to claim 3, further comprising:
generating an image of the tissue at a display; and
generating a three-dimensional thermal image representative of the desired thermal treatment volume at the display.

5. The method for treating tissue according to claim 3, further comprising:
inputting into the electrosurgical generator a distance between the electrode probe assembly and the at least one thermal feedback assembly.

6. The method for treating tissue according to claim 5, further comprising:
inputting into the electrosurgical generator at least one property of the electrode probe assembly.

7. The method for treating tissue according to claim 6, wherein the at least one property of the electrode probe assembly is a length of a treatment portion of the electrode probe assembly.

8. The method for treating tissue according to claim 6, further comprising:
inputting into the electrosurgical generator at least one property of the tissue.

9. The method for treating tissue according to claim 8, wherein the desired thermal treatment volume is estimated based on at least one of the distance between the electrode probe assembly and the at least one thermal feedback assembly, the measured temperature, the at least one property of the electrode probe assembly, or the at least one property of the tissue.

10. The method for treating tissue according to claim 9, wherein the desired thermal treatment volume is estimated based on an Arrhenius model.

11. The method for treating tissue according to claim 3, wherein estimating the desired thermal treatment volume includes estimating at least one of size, rate of treatment progression, and difference between the desired thermal treatment volume and an actual thermal treatment volume.

12. The method for treating tissue according to claim 1, wherein insertion of the electrode probe assembly further includes inserting a plurality of thermal feedback assemblies into tissue, the plurality of thermal feedback assemblies being disposed in the hub symmetrically about the electrode probe assembly.

13. A method for treating tissue, comprising:
inserting an electrode probe assembly and a plurality of thermal feedback assemblies into tissue, the electrode probe assembly being disposed in a hub and the plurality of thermal feedback assemblies being disposed in the hub symmetrically about the electrode probe assembly;
activating an electrosurgical generator coupled to the electrode probe assembly and the plurality of thermal feedback assemblies to deliver electrosurgical energy to the tissue through the electrode probe assembly to thermally treat the tissue;
measuring a temperature of the tissue at each of the plurality of thermal feedback assemblies; and
transmitting the measured temperature from each of the plurality of thermal feedback assemblies to the electrosurgical generator.

14. The method for treating tissue according to claim 13, further comprising:
estimating a desired thermal treatment volume in response to thermal treatment of the tissue based on the measured temperature at each of the plurality of thermal feedback assemblies.

15. The method for treating tissue according to claim 14, further comprising:
inputting into the electrosurgical generator a distance between the electrode probe assembly and each of the plurality of thermal feedback assemblies.

16. The method for treating tissue according to claim 15, further comprising:
inputting into the electrosurgical generator at least one property of the electrode probe assembly.

17. The method for treating tissue according to claim 16, further comprising:
inputting into the electrosurgical generator at least one property of the tissue.

18. The method for treating tissue according to claim 17, wherein the desired thermal treatment volume is estimated based on at least one of the distance between the electrode probe assembly and each of the plurality of thermal feedback assemblies, the measured temperature, the at least one property of the electrode probe assembly, or the at least one property of the tissue.

19. The method for treating tissue according to claim 14, wherein estimating the desired thermal treatment volume includes estimating at least one of size, rate of treatment progression, and difference between the desired thermal treatment volume and an actual thermal treatment volume.

* * * * *